US012216098B2

(12) United States Patent
Heise et al.

(10) Patent No.: US 12,216,098 B2
(45) Date of Patent: Feb. 4, 2025

(54) APPARATUS FOR PROCESSING A LIQUID COMPRISING A TARGET SUBSTANCE

(71) Applicant: Fujifilm Diosynth Biotechnologies UK Limited, Billingham (GB)

(72) Inventors: Charles Heise, Billingham (GB); Jonathan Haigh, Billingham (GB); Tibor Nagy, Billingham (GB); James Pullen, Billingham (GB); Andrew Topping, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 1003 days.

(21) Appl. No.: 16/969,690

(22) PCT Filed: Feb. 11, 2019

(86) PCT No.: PCT/GB2019/050351
§ 371 (c)(1),
(2) Date: Aug. 13, 2020

(87) PCT Pub. No.: WO2019/158906
PCT Pub. Date: Aug. 22, 2019

(65) Prior Publication Data
US 2021/0033574 A1    Feb. 4, 2021

(30) Foreign Application Priority Data

Feb. 16, 2018 (GB) ...................................... 1802593

(51) Int. Cl.
*G01N 30/46* (2006.01)
*C07K 1/34* (2006.01)
(Continued)

(52) U.S. Cl.
CPC ............. *G01N 30/462* (2013.01); *C07K 1/34* (2013.01); *C12N 15/1017* (2013.01); *G01N 30/34* (2013.01)

(58) Field of Classification Search
CPC ........ G01N 30/462; G01N 30/34; C07K 1/34; C12N 15/1017; C12N 15/101;
(Continued)

(56) References Cited

U.S. PATENT DOCUMENTS

2005/0273203 A1   12/2005   Bellafiore et al.
2006/0233665 A1   10/2006   Sasaki et al.
(Continued)

FOREIGN PATENT DOCUMENTS

JP   2006300548 A   11/2006
JP   2006320218 A   11/2006
(Continued)

OTHER PUBLICATIONS

Aug. 22, 2018 (WO) Written Opinion of the International Searching Authority issued in respect of International Application No. PCT/GB19/050351.
(Continued)

*Primary Examiner* — Madeline Gonzalez
(74) *Attorney, Agent, or Firm* — Banner & Witcoff, Ltd.

(57) ABSTRACT

Apparatus for processing a liquid comprising a target substance, preferably a biomolecule, is provided. The apparatus comprises at least a first and a second means for carrying out a unit operation, each means for carrying out a unit operation comprising a feed for a liquid in fluid connection with the inlet of a flow-controller comprising a variable flow inlet valve and an outlet, wherein at least one of the means for carrying out a unit operation comprises feeds for at least two liquids, the feeds being in fluid connection with the inlets of a multiple inlet flow-controller comprising two or more
(Continued)

variable flow inlet valves for dosing the at least two liquids, the flow-controller also comprising an outlet; a feed for a liquid feedstock comprising the target substance in fluid connection with the outlet from the flow-controller thereby to enable combination of the feed for a liquid comprising the target substance with the mixed bioprocessing liquids to produce a device feed; a device for achieving a processing operation comprising a device inlet and a device outlet, the device inlet being in fluid connection with the device feed; and a means for imparting flow through the flow controller and from the feed for the liquid feedstock through the processing device via the device inlet; and wherein the feed for a liquid feedstock comprising the target substance for the second means for carrying out a unit operation comprises the outlet from the first means for carrying out a unit operation.

8 Claims, 4 Drawing Sheets

(51) Int. Cl.
*C12N 15/10* (2006.01)
*G01N 30/34* (2006.01)

(58) Field of Classification Search
CPC ....... B01D 61/14; C12M 47/12; C12M 27/02; C12M 29/18; C12M 29/20; C12M 41/44
USPC .......... 210/198.2, 650–652, 656, 416.1, 258, 210/252, 260
See application file for complete search history.

(56) References Cited

U.S. PATENT DOCUMENTS

| | | | |
|---|---|---|---|
| 2007/0272605 A1 | 11/2007 | Lundblad et al. | |
| 2011/0073548 A1* | 3/2011 | Williams ........... | B01D 15/1871 210/102 |
| 2013/0260419 A1 | 10/2013 | Ransohoff et al. | |
| 2015/0064769 A1 | 3/2015 | Xenopoulos | |
| 2018/0339244 A1 | 11/2018 | Hubbuch et al. | |

FOREIGN PATENT DOCUMENTS

| | | |
|---|---|---|
| JP | 2010227031 A | 10/2010 |
| JP | 2013506127 A | 2/2013 |
| RU | 2600871 C2 | 10/2016 |
| WO | 2011037522 A1 | 3/2011 |
| WO | 2017118835 A1 | 7/2017 |
| WO | 2017118836 A1 | 7/2017 |

OTHER PUBLICATIONS

Aug. 27, 2020 (WO) International Preliminary Report on Patentability issued in respect of International Application No. PCT/GB19/050351.
Oct. 31, 2022 (EP) Communication pursuant to Art. 94(3) EPC issued in respect of EP Application No. 19705809.2.
Feb. 22, 2023 (JP) Notice of Reasons for Refusal issued in respect of JP Application No. 2020-543620.
Nov. 22, 2023 (JP) Decision of Refusal issued in respect of JP Application No. 2020-543620.
Nov. 10, 2023 (KR) Notice of Non-Final Rejection issued Nov. 10, 2023 in respect of KR Application No. 2020-7023167.
Nov. 4, 2023 (SG) Search Report issued in respect of SG Application No. 11202007458Q.
2023 Apr. 2023 (SG) Office Action issued in respect of SG Application No. 11202007458Q.
Aug. 16, 2022 (RU) Search Report issued in respect of RU Application No. 2020130056.
Aug. 18, 2022 (RU) Office Action issued in respect of RU Application No. 2020130056.
Oct. 9, 2023 (RU) Office Action issued in respect of RU Application No. 2020130056.
Feb. 16, 2022 (IN) Office Action issued in respect of IN Application No. 202017033718.
Dec. 6, 2023 (IN) Hearing notice issued in respect of IN Application No. 202017033718.
Pre-Appeal Re-examination Report issued Jun. 26, 2024 in respect of JP Application No. 2020-543620.

* cited by examiner

APPARATUS FOR PROCESSING A LIQUID COMPRISING A TARGET SUBSTANCE

RELATED APPLICATIONS

This application is a National Stage Application under 35 U.S.C. 371 of co-pending PCT application PCT/GB2019/050351 designating the United States and filed Feb. 11, 2018; which claims the benefit of GB application number 1802593.2 and filed Feb. 16, 2018 each of which are hereby incorporated by reference in their entireties.

FIELD

The present invention concerns methods and apparatus for processing liquids comprising a target substance, particularly liquids comprising a biomolecule, and especially recombinant polypeptides.

BACKGROUND

Many biomolecules, especially recombinant polypeptides and nucleic acids, such as plasmids (pDNA), have attracted much attention in particular for therapeutic applications. Such biomolecules are commonly produced by culturing recombinant host cells which have been engineered to express the desired biomolecule. The biomolecule is then recovered from the culture medium by methods typically comprising a number of unit operations. These unit operations commonly include one or more chromatographic purifications, viral inactivation, filtration (including viral, depth and absolute filtration), refolding and ultrafiltration/diafiltration.

Apparatus for processing a solution comprising a target substance is known in the art. However, apparatus for use in the commercial manufacture of such compounds is extremely bulky, and requires extensive floor space and infrastructure. Additionally, whilst some commonality of apparatus can be achieved for several of the unit operations, the designs of apparatus for certain unit operations, such as viral inactivation and/or ultrafiltration differ substantially from those for, for example, chromatographic purification. This means that either more space is required to accommodate two or more sets of apparatus, or that the interoperability and control of the apparatus for the stages is inordinately complex. Further, operators require training on each of the different types of apparatus employed. Accordingly, simplified and broadly-applicable apparatus would be desirable. It would also be desirable to identify apparatus enabling multiple processing steps to be carried out employing a common flow path.

SUMMARY

According to a first aspect of the present invention, there is provided apparatus for processing a liquid comprising a target substance, said apparatus comprising at least a first and a second means for carrying out a unit operation, each means for carrying out a unit operation comprising:
  (i) a feed for a liquid in fluid connection with the inlet of a flow-controller comprising a variable flow inlet valve and an outlet, wherein at least one of the means for carrying out a unit operation comprises feeds for at least two liquids, the feeds being in fluid connection with the inlets of a multiple inlet flow-controller comprising two or more variable flow inlet valves for dosing the at least two liquids, the flow-controller also comprising an outlet;
  (ii) a feed for a liquid feedstock comprising the target substance in fluid connection with the outlet from the flow-controller thereby to enable combination of the feed for a liquid comprising the target substance with the mixed bioprocessing liquids to produce a device feed;
  (iii) a device for achieving a processing operation comprising a device inlet and a device outlet, the device inlet being in fluid connection with the device feed; and
  (iv) a means for imparting flow through the flow controller and from the feed for the liquid feedstock through the processing device via the device inlet;
wherein the feed for a liquid feedstock comprising the target substance for the second means for carrying out a unit operation comprises the outlet from the first means for carrying out a unit operation.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DETAILED DESCRIPTION

Figure 1:
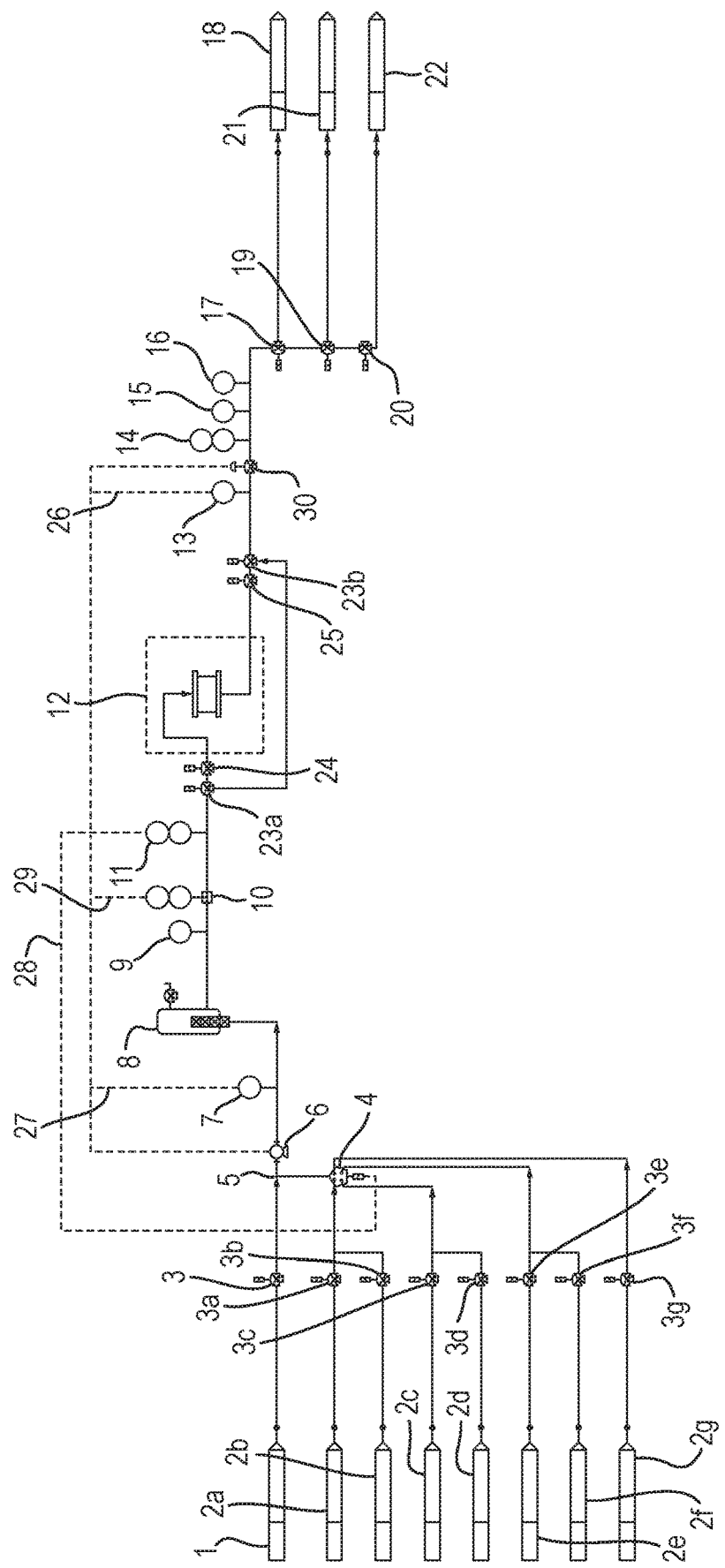
FIG. 1 depicts a diagram of an apparatus for performing a bioprocessing operation.

In some embodiments, the apparatus comprises two means for carrying out a unit operation. In other embodiments, the apparatus comprises three, four, five, six, seven, eight, nine or more means for carrying out a unit operation, preferably each having the features described above for the first and second means. In many preferred embodiments, the means for carrying out a unit operation are connected in series, with the feed for a liquid feedstock comprising the target substance for a subsequent means for carrying out a unit operation comprising the outlet from the preceding means for carrying out a unit operation. In many highly preferred embodiments, each unit operation differs from the other unit operations.

In certain embodiments, each means for carrying out a unit operation comprises substantially the same flow path.

Means for imparting flow of the liquids are well known in the art, and include the application of gas pressure to the liquid, especially an inert gas, such as nitrogen or helium. Preferably the means for imparting flow of the liquid comprises one or more pumps. Pumps which can be employed include peristaltic, diaphragm, lobe and centrifugal pumps. Both disposable and re-usable pump designs can be employed. In many preferred embodiments, a single pump is employed for each means of carrying out a unit operation, located downstream of the fluid connection between the connection between the feedstock and the outlet from the flow-controller. Most preferably the pump is located upstream of the bioprocessing device. The type and size of the pump selected is commonly dependent on the flow capacity and pressure profile appropriate to the scale and design parameters of the apparatus. In certain highly preferred embodiments, the pump is a quaternary diaphragm pump.

The flow-controller comprises variable flow, preferably intermittent flow, inlet valves which regulate the flow of liquid through the flow-controller. The multiple inlet flow-controller comprises at least 2 inlet valves and in many instances comprise up to 8, such as 3, 4, 5, 6 or 7, inlet valves. The inlet valves may each have the same dimensions, or one or more of the inlet valves may have different dimensions. In certain preferred embodiments, the volume measured from each inlet valve to the outlet of the flow-controller is the same for each inlet, and it is highly preferred that both the volume and the path length measured from each inlet valve to the outlet of the flow-controller is the same for each inlet. In many embodiments, each means for carrying out a unit operation preferably comprises a multiple inlet flow controller.

The flow-controller employed in the present invention also comprises at least one outlet, and whilst two or more outlets may be present, it is preferred that a single outlet is employed.

The variable flow valves may regulate the flow between a first, relatively low flow rate wherein the liquid remains able to flow and at least a second, higher flow rate. In preferred embodiments, the variable flow valve is an intermittent flow valve, which prevents flow in a first position, but permits flow in at least a second position. Most preferably, all of the valves are intermittent flow valves. The valves may comprise actuators known in the art, such as pneumatic or, preferably, solenoid actuators.

Preferably the variable flow valves are controlled, most preferably by a programmable control unit, to regulate the opening and closing of the valves in order to achieve the required relative quantities of the input liquids flowing through the multiple inlet flow-controller. This is preferably achieved through cycling, with a pre-determined time period or cycle rate, through the inlet valves in the flow-controller and regulating the opening or closing of the valve according to the required proportion of the cycle time to generate the desired composition. The cycle rate can be either constant or varied. Most preferably, intermittent flow inlet valves are employed, and are controlled such that in operation, only one valve is open at any given time. In many embodiments, the cycle rate of the multiple inlet flow-controller is maintained as a constant and the desired relative quantities of the input liquids remains consistent.

In many embodiments, multiple cycles are employed. The number of cycles employed will depend on numerous factors such as the duration of the process, the volume of liquid being processed, the flow rate and the maximum operating pressure of the apparatus. In certain embodiments, at least 10 cycles, such as at least 50, 100, 500, 750, 1000, 1500, 2000, 3000, 5000, 7500, 10000 or more cycles can be employed.

It will be recognised that a range of cycle frequencies can be employed. In many instances, the frequency is less than 100 Hz, typically less than 50 Hz, commonly less than 10 Hz, and preferably less than 5 Hz. In certain preferred embodiments, the frequency is 2 Hz or less, most preferably 1 Hz or less, such as from 0.05 to 0.5 Hz.

Whilst mixing may be achieved by simply combining the flows of the target feed and the flow-controller outlet, optionally in combination with the action of a pump, in many preferred embodiments, the apparatus further comprises an in-line mixer, preferably a mixing chamber, preferably comprising a static mixer, most preferably a time-delay, split flow static mixer. In many embodiments, the in-line mixer is located downstream of a pump and upstream of the device for achieving the bioprocessing operation. In some preferred embodiments, the in-line mixer also comprises a bubble trap.

Unit operations that can be carried out by the device for achieving a processing operation are most preferably bioprocessing operations. Bioprocessing operations include chromatography, viral inactivation, filtration, refolding, ultrafiltration, diafiltration, microfiltration, in-line conditioning and refolding.

Chromatography operations that can be carried out using the apparatus of the present invention include affinity chromatography, ion-exchange (either or both anion and cation exchange) chromatography, hydrophobic interaction chromatography (HIC), reverse-phase chromatography, expanded bed chromatography, mixed-mode chromatography, membrane chromatography and size exclusion chromatography (SEC). In many embodiments, Protein A affinity chromatography comprises at least one of the unit operations. Devices for carrying out the chromatography operations comprise the appropriate chromatography apparatus, such as a membrane, fibre monolith or column. The number and sequence of chromatographic unit operations will be selected according to the nature of the target biomolecule.

Viral inactivation unit operations that can be carried out using the apparatus of the present invention commonly comprise storage vessel in which the liquid comprising the target biomolecule can be stored under conditions for sufficient residence time to inactivate viruses. In certain embodiments the outlet and the inlet of the device can be fluidly connected to generate a re-circulation loop. In one such embodiment the apparatus is set up with a vessel or bag fluidly connected between the "device" inlet and "device" outlet and one of the apparatus outlets is fluidly connected to one of the multiple inlet flow-controller inlets. The vessel or bag between the device "inlet" and "outlet" being fluidly connected to the liquid feedstock inlet is filled by a means to impart flow, typically a pump, or conditioned with at least one other liquid through at least one of the other multiple inlet flow-controller inlets. In certain embodiments the vessel or bag is a mixing vessel or bag. The process liquid is re-circulated through the inlet of the multiple inlet flow-controller to the vessel or bag and back to the inlet of the multiple inlet flow-controller as the solution comprising a target substance is conditioned by at least one additional liquid fluidly connected to at least one other inlet on the multiple inlet flow-controller.

Filtration unit operations that can be carried out include viral, depth and absolute filtration, ultrafiltration, diafiltration and microfiltration. In many embodiments, the filtration unit operation comprises a filter module between the device inlet and device outlet. The filter module is flushed and chased using at least two liquid feeds attached to the multiple inlet flow-controller inlets and the solution comprising a target molecule is fluidly connected to the feedstock inlet. Processing of liquid through the filter is achieved through a means of imparting flow fluidly connected to and positioned downstream of the multiple inlet flow-controller outlet and feedstock inlet, and upstream of the filter module. The filter modules commonly employ configurations, which are well known in the bioprocessing art.

Viral filtration, depth filtration and absolute filtration are unit operations that are well known in the art and can be carried out using the apparatus of the present invention commonly employing filter devices, which are well known in the bioprocessing art. In many embodiments the filter device or devices are placed between the device inlet and outlet, in order to execute a specific unit operation. In other embodiments the filter device is positioned downstream of the apparatus outlet, which in certain embodiments allows the apparatus to perform a main unit operation, such as chromatography, viral inactivation, tangential flow filtration, viral filtration or depth filtration, followed by a secondary filtration operation.

Tangential flow filtration ("TFF") unit operations that can be carried out using the apparatus of the present invention include conventional recirculating TFF and single pass TFF. In certain embodiments the outlet and the inlet of the apparatus can be fluidly connected to generate a re-circulation loop, an example being re-circulating tangential flow filtration. In one embodiment, as known in the art, the apparatus is set up with a TFF module comprising either flat sheet, hollow fibre or spiral wound membranes between the device inlet and device outlet and the retentate from the TFF module is directed from one of the apparatus outlets to a fluidly connected inlet on a vessel or bag, containing at least one inlet and one outlet. The outlet of the vessel or bag is fluidly connected to the liquid feedstock inlet. The vessel or bag is maintained at a constant level using an auxiliary means to supply the feedstock or liquid into the vessel or bag by being fluidly connected to a second inlet on the vessel or bag. In another embodiment, the apparatus is set up with a TFF module comprising either flat sheet, hollow fibre or spiral wound membranes between the device inlet and device outlet and the retentate from the TFF module is fluidly connected from one of the apparatus outlets back to one of the inlets of the multiple inlet flow-controller valve. In certain embodiments the re-circulation loop from the apparatus outlet to its inlet contains a break vessel or bag. A solution comprising a target substance or a liquid is drawn into the re-circulation loop through the liquid feedstock inlet by a means for imparting flow, typically a pump. The retentate is re-circulated through the TFF module, preferably through one of the multiple inlet flow-controller inlets. The multiple inlet flow-controller may be employed to mix the retentate with at least one other liquid. Operation of recirculating TFF is well known in the art and is controlled through setting a cross-flow rate and transmembrane pressure.

In certain embodiments single pass TFF can be configured with a TFF module comprising either flat sheet, hollow fibre or spiral wound membranes between the device inlet and device outlet for example, as in the case of single pass TFF as described in WO2017/118835.

In some embodiments a hybrid of single pass and re-circulating TFF can be employed, where the retentate generated using a variable flow valve downstream of the TFF module is returned to the feed vessel.

Apparatus according to the present invention commonly additionally comprises one or more of bubble traps, pressure sensors, temperatures sensors, pH sensors, flow rate sensors, conductivity sensors, air sensors, and uv sensors, such as a uv/visible multi-wavelength sensor. One or more of each of the foregoing may be present.

In one particular embodiment of the present invention, there is provided apparatus for processing a liquid comprising a target substance, said apparatus comprising:
(i) feeds for at least two liquids;
(ii) a multiple inlet flow-controller comprising two or more variable flow inlet valves for mixing at least two liquids, the flow-controller also comprising a single outlet;
(iii) a feed for a liquid feedstock comprising the target substance in fluid connection with the outlet from the flow-controller;
(iv) a means for imparting flow, typically by use of a pump, through the flow controller and from the feed for the liquid feedstock through the processing apparatus via the feed inlets;
(v) a device for mixing of the at least two liquids;
(vii) a device for trapping air bubbles from the process liquids
(vii) a common flowpath for achieving a processing operation comprising a device inlet and a device outlet, the device inlet being in fluid connection with the feed inlets;
(viii) the device inlet and outlet being in fluid connection with modules used for chromatography, filtration (including viral filtration), tangential flow filtration, single pass tangential flow filtration, refold and viral inactivation;
(ix) a means to bypass the device inlet and outlet;
(x) a means downstream of the device outlet to regulate the pressure;
(xi) a number of sensors appropriate for monitoring the processing operation upstream and downstream of the device inlet and device outlet; and
(xii) at least one outlet in fluid connection with the feed inlets.

The apparatus according to the present invention preferably comprises a means for additional pressurising of the processing device located downstream of the device. Means for imposing pressure are known in the art and include pinch valves, diaphragm valves, especially variable position diaphragm valves.

In many embodiments, the device for mixing the liquids and the device for trapping air bubbles comprise a single device.

In certain embodiments the apparatus comprises a multi-use flow path constructed from materials, such as stainless steel, that allow significant number of re-uses before replacement is required.

In certain embodiments the apparatus comprises a single-use flow path constructed from materials, such as plastics, that are designed with a limited lifetime and utilised as a disposable consumable.

In many embodiments, each unit operation is operated under the control of a programmable control unit, preferably a computer. In some embodiments, a single control unit controls two or more unit operations. In other embodiments, each unit operation is under the control of a separate control unit. In these other embodiments, preferably each control unit employs a common programming language, which enables simplified communication between control units.

According to a second aspect of the present invention, there is provided apparatus for preparing a liquid mixture, said apparatus comprising:
(i) feeds for at least two liquids;
(ii) a multiple inlet flow-controller comprising two or more variable flow inlet valves for dosing at least two liquids, the flow-controller also comprising an outlet;
(iii) a pump for imparting flow through the flow-controller and from the feed for the liquid feedstock through the bioprocessing apparatus via the feed inlets;
(iv) a static mixer for in-line mixing of the at least two liquids; and
(v) an outlet for the liquid mixture;
wherein the pump is upstream of the device for in-line mixing, and both the pump and the device for in-line mixing are located downstream of the multiple inlet flow.

Feeds for liquids, multiple inlet flow controllers, pumps and static mixers that can be employed in the second aspect are as described above in respect of the first aspect of the present invention.

The apparatus of the second aspect can be employed for the preparation of liquid mixtures, preferably solutions, such as buffer solutions, such as by mixing acid and/or salt solutions, commonly for use in processing operations, and especially bioprocessing operations. The solutions may be stored prior to use, for example in a processing operation, especially a bioprocessing operation, or may be used directly, for example by fluidly connecting the outlet for the liquid mixture to the device using the mixture.

The apparatus of the second aspect of the present invention may comprise additional elements as described above for the first aspect of the present invention, especially one or more of bubble traps, pressure sensors, temperatures sensors, pH sensors, flow rate sensors, conductivity sensors, air sensors, and uv sensors, such as a uv/visible multi-wavelength sensor. One or more of each of the foregoing may be present.

The apparatus of the second aspect of the present invention preferably comprises a single pump. In certain highly preferred embodiments, the pump is a quaternary diaphragm pump.

The static mixer employed in the apparatus of the second aspect of the present invention, is preferably a time-delay, split flow static mixer.

In many embodiments, the apparatus of the second aspect of the present invention is operated under the control of a programmable control unit, preferably a computer.

The apparatus of the second aspect of the present invention can advantageously be operated without the necessity to incorporate complex feedback mechanisms to regulate the composition of the liquid being produced.

Liquids that can be employed with the apparatus of the present invention include those known in the art for carrying out the appropriate processing unit operation. Examples includes acidic, neutral and basic solutions, such as those having a pH in the range of from 2.5 to 14, for example sodium potassium or ammonium hydroxide solutions, phosphoric, sulphuric, hydrochloric or acetic acid solutions; salt solutions, such as solutions having a salt concentration of up about 3M, including sodium, calcium, potassium, and ammonium salts, for examples phosphate, chloride, acetate, citrate and sulphate salts; buffer solutions, examples of which are well known in the art; reductants (eg. DTT and TCEP); amino acids (eg. histidine, arginine, glycine); detergents (eg. Tween 20, Triton-X100) and water-miscible solvents such as polyols, for example glycerol and PEG; and mixtures of one or more of the foregoing.

Biomolecules which can be processed using the present invention include, for example pDNA; cellular therapies, vaccines, such as viral vaccines, gene therapy products, sugars, inclusion bodies, particularly inclusion bodies comprising polypeptides; and especially recombinant polypeptides.

pDNA may be in one or more of multiple forms, such as supercoiled, linear and open-circular (i.e. nicked or relaxed) isoforms. Supercoiled pDNA isoform has a covalently closed circular form and the pDNA is negatively supercoiled in the host cell by the action of host enzyme systems. In the open-circular isoform, one strand of the pDNA duplex is broken at one or more places.

Methods for the production of pDNA are well known in the art. pDNA may be natural or artificial, for example, cloning vectors carrying foreign DNA inserts. In many embodiments, the pDNA is in the size range of 1 kilobase to 50 kilobases. For example pDNA encoding expressed interfering RNA is typically in the size range of 3 kilobases to 4 kilobases.

Polypeptides, especially recombinant polypeptides, include therapeutic proteins and peptides, including cytokines, growth factors, antibodies, antibody fragments, immunoglobulin like polypeptides, enzyme, vaccines, peptide hormones, chemokines, receptors, receptor fragments, kinases, phosphatases, isomerases, hydrolases, transcription factors and fusion polypeptides.

Antibodies include monoclonal antibodies, polyclonal antibodies and antibody fragments having biological activity, including multivalent and/or multi-specific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Inclusion bodies include insoluble aggregates formed in the cytoplasm of bacterial cells such as *E. coli*, most commonly comprising polypeptide and especially recombinant polypeptide.

Methods for processing a biomolecule, such as a recombinant polypeptide, and most especially purifying or isolating a recombinant polypeptide, form further aspects of the present invention.

One embodiment of apparatus according to the present invention is described with reference to FIG. 1 A first device for performing a bioprocessing operation comprises a feed for a liquid comprising a target biomolecule, 1, and feeds for six different buffers, 2a to 2f, plus water for injection, 2g are provided. Each feed is fitted with a valve, such as straight-through diaphragm valve, 3 and 3a to 3g to enable the flow to be switched on or off. In the embodiment shown, buffer feeds 2a and 2b, 2c and 2b and 2d and 2e are combined downstream of the valves, 3a to 3f respectively, to form three buffer feed lines, which are fluidly connected, along with the water for injection feed, 2g to different inlets on a multiple inlet flow controller, 4, comprising a four valve manifold with a single outlet having a fast acting solenoid actuator. By this configuration, and by appropriate opening and closing of valves 3a and 3b, 3c and 3d, and 3e and 3f, allows selection between buffers 2a and 2b, 2c and 2d or 2e and 2f, thereby increasing the flexibility of operation of the apparatus. The outlet from the multiple inlet flow controller, 4, is in fluid connection with the feed for a liquid comprising a target biomolecule, 1, at 5, upstream of a pump, 6, which imparts flow of the combined feeds through a static mixer fitted with a bubble trap, 8, and to the inlet of first chromatography column, 12. The line feeding the output from the pump, 6, to the chromatography column, 12, is fitted with a pressure sensor, 7, air sensor, 9, a flow meter, 10, such as an ultrasonic flow meter and a combined temperature and conductivity sensor, 11. In some embodiments, the pump, 6, is controlled via a programmable control unit in response to a feedback signal, 29, from the flow meter, 10. In some embodiments, optionally, the multiple-inlet flow controller, 4, is controlled via a programmable control unit in response to a feedback signal, 28, from the conductivity and temperature sensor, 11. The outlet line from the chromatography column, 12, is provided with pressure sensor, 13, a combined temperature and conductivity sensor, 14, a uv detector, such as a uv/visible multi-wavelength detector, 15, a pH meter, 16, and a variable position valve, 30, which can be employed to regulate pressure and to impose back pressure if desired. Preferably, the operation of the pump, 6, and the variable position valve, 30, and thereby the regulation of the pressure in the apparatus, are controlled via a programmable control unit in response to feedback signals, 26 and 27, from the pressure sensors, 7 and 13. The outlet line passes through a series of valves, 17, 19 and 20, which enable the flow to be controlled between an exit feed, 18, a feed to waste, 21, or an outlet feed, 22, for example enabling collection or sampling. The apparatus is further fitted with valves, 23a and 23b, which enable the flow to be diverted to bypass the column, 12, if required during operation, and further valves, 24 and 25, which enable flow through the column to be halted. The exit feed, 18, can then be employed as the feed line comprising a target biomolecule in a second device for performing a bioprocessing operation, configured as illustrated in FIG. 1, but where preferably the chromatography column, 12, is replaced with a different means for performing a unit operation, such as a different type of chromatography, or a non-chromatographic unit operation, and wherein in the second device for performing a unit operation, the feed, 1, comprises the exit feed, 18, from the first means for performing a unit operation.

In one method of operation, valve 3 is opened, whilst valves 3a to 3g are closed, and the liquid comprising the biomolecule is fed by the pump, 6, to the column, 12, to load the column with the biomolecule, for example where the biomolecule is a monoclonal antibody, a column comprising Protein A affinity resin, such that the monoclonal antibody selectively binds to the Protein A resin. On completion of the desired loading, valve 3 is closed, and one or more of valves 3a to 3g is opened, to enable one or more of the bioprocessing liquids 2a to 2g to be pumped through the column, 12. In some embodiments, initially only valve 3a is opened, and multiple-inlet valve 4 is operated so as to open the inlet valve to which buffer 2a, which may be a wash buffer, is supplied, such that the loaded column is washed with the buffer, 2a. On completion of the desired washing stage, one or more of valves 3b to 3g may be opened, with valve 3a either remaining open or being closed. The inlet valves on the multiple inlet valve, 4 are opened in order to allow the bioprocessing liquids 2b to 2g, or mixtures thereof to be pumped through the column, 12. By controlling the opening and closing of the valves on the multiple inlet valve, 4, and/or the valves 3a to 3g, the composition of the bioprocessing liquid fed to the column can be altered and controlled as desired. For example, where valves 3b, 3c and 3e are open, changing the inlet valve which is open in the multiple-inlet flow controller, 4, and closing the others, enables the composition of the liquid fed to be changed in stepwise fashion. In another example, two or more of the inlet valves of the multiple-inlet flow controller, 4 can be opened and closed at a given frequency, and for a chosen period of time to enable a given mixture of the bioprocessing liquids to be fed to the column, 12. Adjustment of the times and/or frequency that the inlet valves on the multiple inlet valve, 4, are open or closed, allows the composition of the liquid fed to the column to be altered. Where the times and/or frequency are altered in stepwise fashion, the composition also changes in a stepwise manner. Where the times and/or frequency are altered gradually over a period of time, the composition also changes gradually, enabling the application of a gradient to the column, 12. By whichever desired method, the liquid composition fed to the column is changed to a composition which causes the biomolecule to elute from the column. Prior to elution, liquids exiting from the column, 12 are either collected via the outlet, 22, or sent to waste, 21, and valves 17, 19 and 20 are set accordingly. For elution of the biomolecule, valves 19 and 20 are closed, and valve 17, opened, allowing the biomolecule to pass to the second unit operation, 18.

Operation of the second means for performing a unit operation can be substantially as described above with respect of the first unit operation. It will be recognised that the biomolecule exiting the second means for performing a unit operation through the exit line equivalent to exit line of the first means for performing a unit operation, 18, may either be recovered and used as is, or may be subject to one or more further unit operations. Such further unit operations may employ conventional apparatus, or further apparatus according to the configuration illustrated in FIG. 1, or otherwise according to the present invention.

The present application is illustrated without limitation by the following example.

In a chromatography process operation, a protein is bound to chromatography resin, washed with buffers of differing salt concentration and then removed (eluted) by using a high salt concentration buffer. As an example, recombinant Lactoferrin was bound to and eluted from a 2.3 L POROS-XS cation exchange resin column using pH 7.5 sodium phosphate buffers with sodium chloride concentrations from 0 to 1M. This was performed on a single stand-alone unit with a fully disposable flowpath that contained the features described in FIG. 1, except that valve 23b was replaced with a simple fluid connection. Stock solutions were attached to the inlets in the following order: 2M sodium chloride was attached to inlet 2a; 0.1M dibasic sodium phosphate was attached to inlet 2c; 0.01M monobasic sodium phosphate was attached to inlet 2e; water was attached to inlet 2g; and the protein feed was attached to the sample inlet, 1. Buffers were generated through proportionally selecting each of the stock solutions to produce the desired buffer composition through the action of the multiple inlet flow controller, 4, and the downstream pump, 6, and the static mixer, 8. During the establishment of the correct buffer composition, the column, 12, was by-passed through valve 23a, with valves 24 and 25 closed, the unwanted buffer being directed to the waste, 21. Once the buffer was homogeneous, as indicated by a steady reading from the upstream conductivity sensor, 11, the buffer was supplied to the chromatography column, 12, through opening valves 24 and 25 and closing the by-pass line at valve 23a. The process conditions were monitored using the conductivity, UV and pH sensors, 14, 15 and 16, downstream of the column, 12. During the conditioning of the column ahead of the binding of the protein to the column and post-use water rinse the liquid was directed to waste, 21. Once conditioned, the chromatography resin was loaded with protein drawn in through the sample inlet, 1, by the action of the pump, 6, pushed through the static mixer, 8, on onto the column, 12. The flowthrough from the column was collected through the exit feed, 18, whilst the first low salt buffer wash was collected through the outlet feed, 22, and the second medium salt buffer wash was collected through the exit feed, 18. Finally, the protein was recovered from the column using the high salt elution buffer and collected through the outlet feed, 22.

Figure 2:
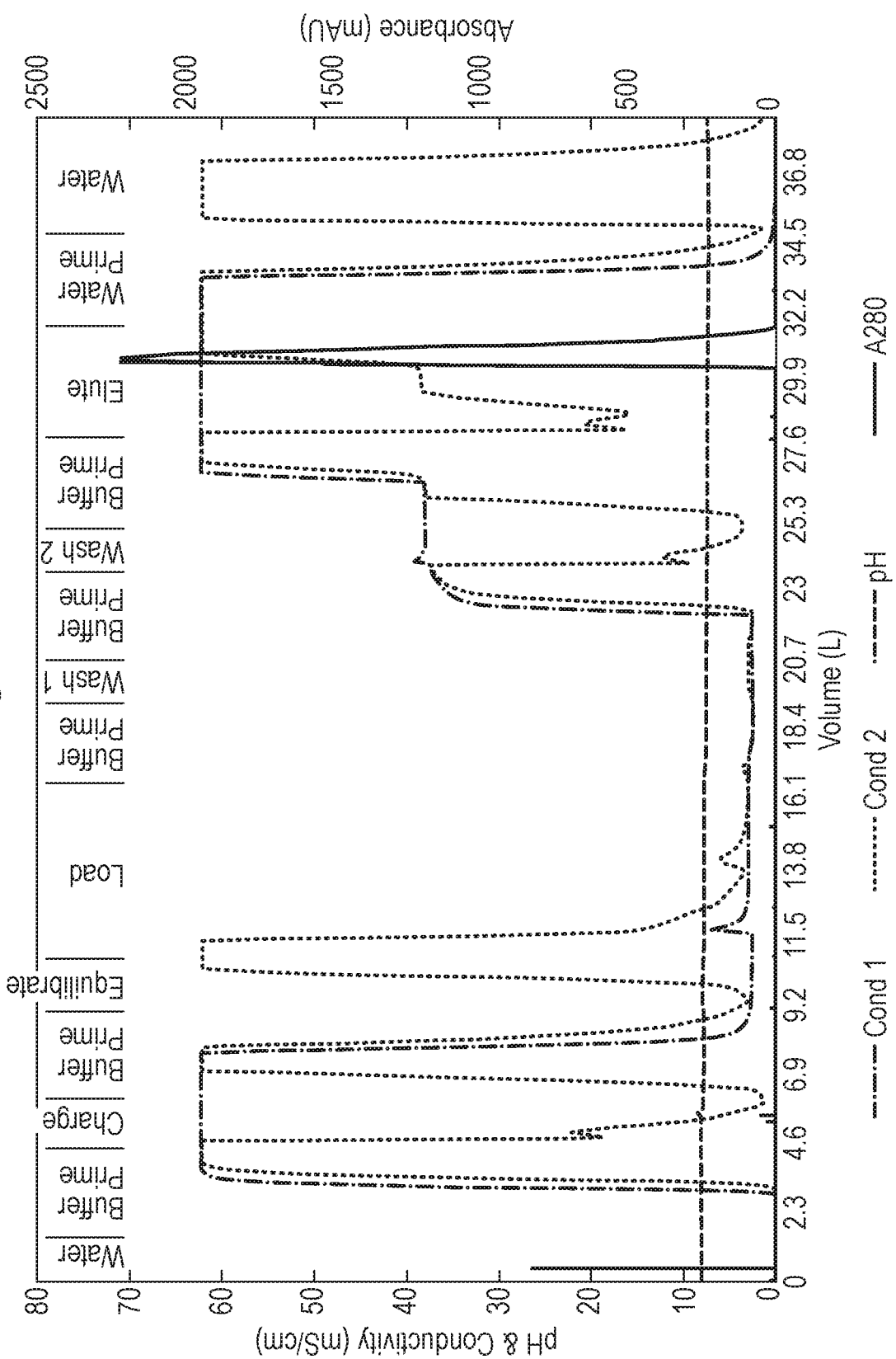
FIG. 2 is a graph depicting data for conductivity, pH and A280 absorbance.
Figure 3:
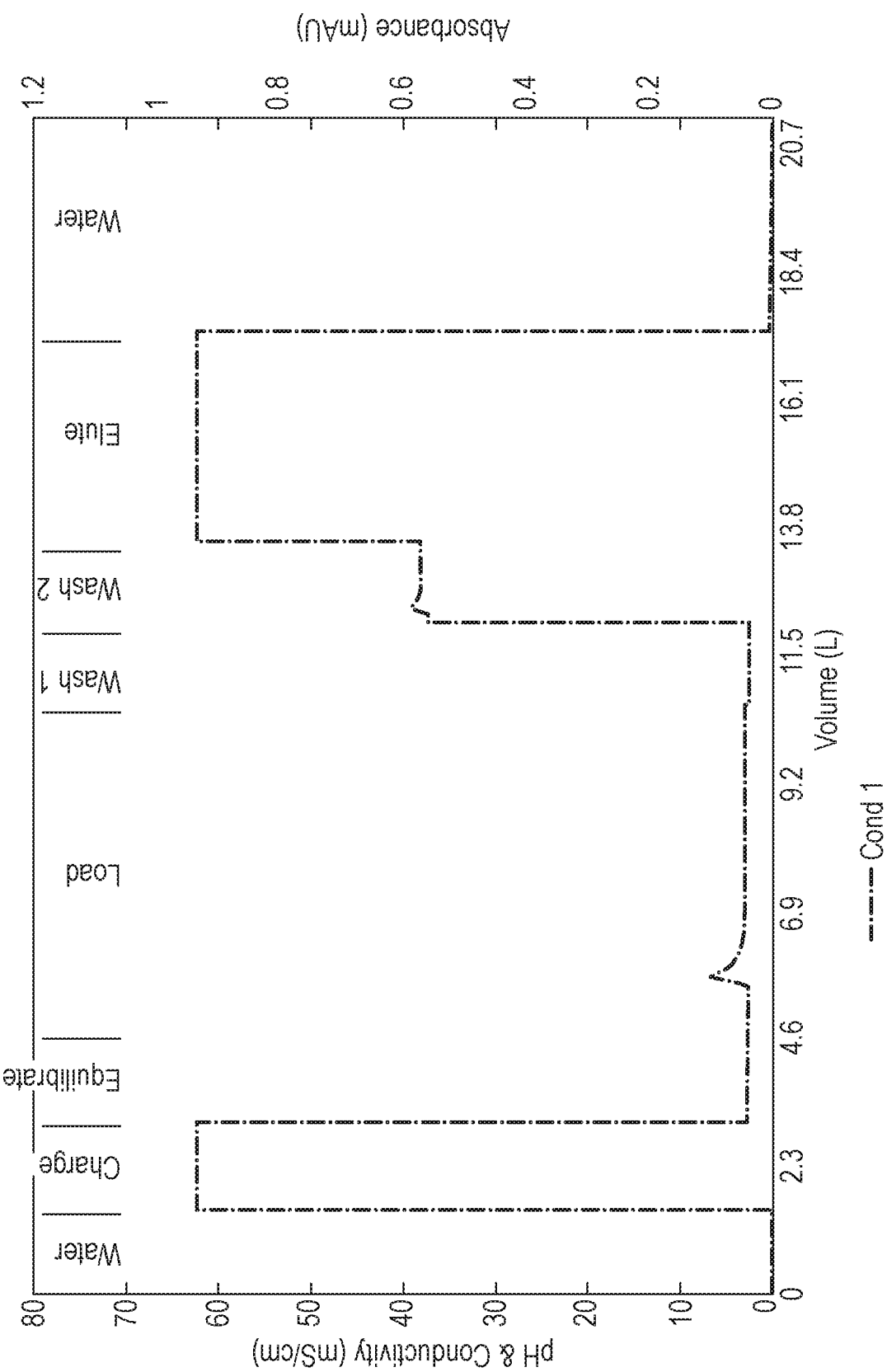
FIG. 3 is graph depicting data for conductivity.
Figure 4:
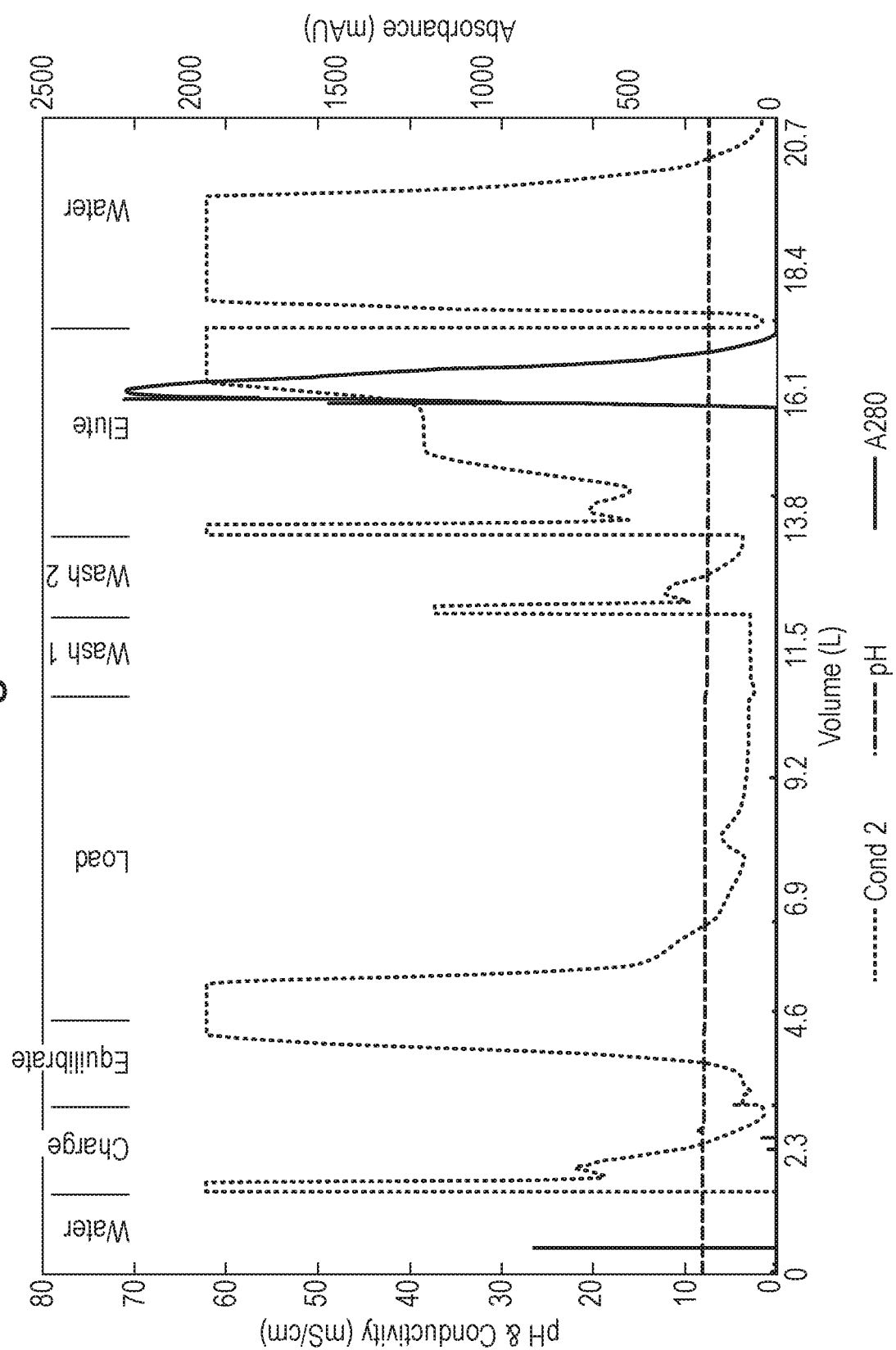
FIG. 4 is a graph depicting data for conductivity, pH and A280 absorbance.

Three processing buffers were generated from the 4 stock solutions attached to the system: 25 mM sodium phosphate pH 7.5±0.1 (low salt); 25 mM sodium phosphate, 0.5M sodium chloride pH 7.5±0.1 (medium salt) and 25 mM sodium phosphate, 1.0M sodium chloride pH 7.5±0.1 (high salt) using specific ratios of salt, acid, base and water as listed in Table 1. The chromatography column was charged (high salt), equilibrated (low salt), washed (low salt and medium salt) and eluted (high salt) at 31 L/h, using the four stock concentrates. 3 L 0.8 g/L Lactoferrin in 25 mM sodium phosphate pH 7.5 was loaded onto the column and chased with 2 L pre-made 25 mM sodium phosphate at 15 L/h. The results of the run are shown in FIGS. 2 to 4. FIG. 2 shows the sensor readings for conductivity, pH and $A_{280}$ absorbance for the whole run, including the buffer prime blocks when the column was placed in by-pass. FIG. 3 shows the conductivity of the buffers pumped onto the column, indicating the in-line buffer conditioning works successfully. FIG. 4 shows the conductivity, pH and $A_{280}$ absorbance post column. FIG. 4 shows that there is an expected residual flush out of the buffer from the by-pass to the sensors and a delay before the new buffer passes through the column, given by the sharp conductivity rises and stepped falls. The critical stage is the elution step, where the column transitions from the washes to the high salt and successfully removes the bound protein. This demonstrates an advantage of the system; it can generate the correct buffers using real-time in-line conditioning from stock solutions for supply into a unit operation. In this example, the system successfully executed a typical bind-elute chromatography run used for purifying proteins with stock solutions, without the requirement to pre-make all the different processing buffers.

TABLE 1

Conductivity and pH values for in-line conditioned buffers

| Buffer | 2M sodium chloride (%) | 0.1M dibasic sodium phosphate (%) | 0.01M monobasic sodium phosphate (%) | Water (%) | Conductivity (mS/cm) | pH |
|---|---|---|---|---|---|---|
| 25 mM sodium phosphate pH 7.5 | 0 | 20 | 53 | 27 | 2.5 | 7.55 |
| 25 mM sodium phosphate, 0.5M sodium chloride pH 7.5 | 25 | 23 | 22 | 30 | 37.2 | 7.48 |
| 25 mM sodium phosphate, 1.0M sodium chloride pH 7.5 | 50 | 24 | 14 | 12 | 62.3 | 7.42 |

The invention claimed is:

1. An apparatus for processing a liquid comprising a target substance, said apparatus including at least a first means for carrying out a unit operation comprising:
   (i) at least two feed liquids being in fluid connection with inlets of a multiple inlet flow-controller comprising two or more variable flow inlet valves for dosing the at least two feed liquids, the multiple inlet flow-controller also comprising an outlet upstream of a first processing device;
   (ii) a feed for a liquid feedstock comprising the target substance in fluid connection with the outlet from the multiple inlet flow-controller thereby to enable combination of the feed for a liquid comprising the target substance with mixed bioprocessing liquids to produce a device feed upstream of the first processing device;
   (iii) the first processing device for achieving a processing operation comprising a device inlet and a device outlet, the device inlet being in fluid connection with the device feed and producing a first processed liquid feed exiting the first processing device via the device outlet; and
   (iv) a means for imparting flow of the at least two feed liquids through the multiple inlet flow controller and the feed for a liquid feedstock comprising the target substance through the first processing device via the device inlet;
   the apparatus further comprising a second means for carrying out a unit operation comprising a second processing device, wherein the second means for carrying out a unit operation is connected in series to receive the first processed liquid feed from the first means for carrying out a unit operation, and
   wherein the first processing device carries out a different processing function from the second processing device.

2. The apparatus according to claim 1, wherein the unit operation of the first means for carrying out a unit operation and the unit operation of the second means for carrying out a unit operation are selected from chromatography, viral inactivation, filtration, ultrafiltration, diafiltration, microfiltration, in-line conditioning and refolding, in each case where the target substance comprises a recombinant polypeptide.

3. The apparatus according to claim 1, wherein the means for imparting flow comprises a pump, located downstream of a fluid connection between the feed for a liquid feedstock comprising the target substance and the outlet from the multiple inlet flow-controller.

4. The apparatus according to claim 3, wherein the pump is located upstream of the first processing device for achieving a processing operation.

5. The apparatus according to claim 1, further comprising:
(i) a device for ensuring homogeneous mixing upstream of the first processing device;
(ii) a device for trapping air bubbles upstream of the first processing device;
(iii) a means to bypass the first processing device;
(iv) a means downstream of the first processing device outlet to regulate pressure; and
(v) a number of sensors appropriate for monitoring the bioprocessing operation of the apparatus.

6. The apparatus of claim 5 wherein the device for ensuring homogeneous mixing upstream of the first processing device comprises a static mixer.

7. A process for preparing a biomolecule, comprising processing the biomolecule using apparatus according to claim 1.

8. The process according to claim 7, wherein the biomolecule is a recombinant polypeptide.

* * * * *